(12) United States Patent
Danker et al.

(10) Patent No.: US 10,408,816 B2
(45) Date of Patent: Sep. 10, 2019

(54) METHOD AND DEVICE FOR AUTOMATICALLY DETERMINING THE POSITION OF A MICROSYSTEM FOR MANIPULATING A SPHERICAL MICROOBJECT

(71) Applicant: NMI Naturwissenschaftliches und Medizinisches Institut an der Universität Tübingen, Reutlingen (DE)

(72) Inventors: Timm Danker, Tübingen (DE); Elke Guenther, Reutlingen (DE)

(73) Assignee: Multichannel Systems MCS GmbH, Reutlingen (DE)

( * ) Notice: Subject to any disclaimer, the term of this patent is extended or adjusted under 35 U.S.C. 154(b) by 101 days.

(21) Appl. No.: 15/422,271

(22) Filed: Feb. 1, 2017

(65) Prior Publication Data
US 2017/0138927 A1 May 18, 2017

Related U.S. Application Data

(63) Continuation of application No. 14/080,643, filed on Nov. 14, 2013, now abandoned, which is a (Continued)

(51) Int. Cl.
*G01N 33/487* (2006.01)
*G01B 7/004* (2006.01)
(Continued)

(52) U.S. Cl.
CPC ....... *G01N 33/48728* (2013.01); *G01B 7/004* (2013.01); *G01B 7/14* (2013.01);
(Continued)

(58) Field of Classification Search
None
See application file for complete search history.

(56) References Cited

U.S. PATENT DOCUMENTS 6,218,663 B1 * 4/2001 Nisch .............. G01N 1/32
250/307
6,470,226 B1 * 10/2002 Olesen ........... G01N 33/48728
435/287.1

(Continued)

*Primary Examiner* — Ramesh B Patel
(74) *Attorney, Agent, or Firm* — Burns & Levinson LLP; Bruce D. Jobse (57) ABSTRACT

In a method for automated determination of the relative position (x/y/z) between a first hole (27) on a first microsystem component (11), which is preferably provided with a first channel (44) opening in the first hole (27), and at least one second hole (29) on a second microsystem component (12), which is preferably provided with a second channel (45) opening in the second hole (29), the two microsystem components (11, 12) lie in a liquid medium (41) at least in the region (25, 26) of the holes (27, 29). Under the supervision of a control device (15) controlled by a computer (22), the first and second microsystem components (11, 12) are displaced relative to one another into different relative positions (x/y/z). Electrical signals (37) are delivered to one of the two microsystem components (12, 12) and are recorded on the other of the two microsystem components (11, 12) as measurement values (38) which depend on the relative position of the two microsystem components (11, 12) with respect to one another. For different relative positions (x/y/z) between the two microsystem components (11, 12), measurement values (38) are determined, from which the relative position (xn/yn/zn) in which the two microsystem components (11, 12) are to be positioned with respect to one another in such a way that their holes (27, 29) are mutually aligned is ascertained in the control device (15).

21 Claims, 5 Drawing Sheets

Related U.S. Application Data continuation of application No. PCT/EP2011/058122, filed on May 19, 2011.

(51) Int. Cl.
*G01N 35/00* (2006.01)
*G01B 7/14* (2006.01)

(52) U.S. Cl.
CPC .. *G01N 35/00584* (2013.01); *Y10T 29/49004* (2015.01); *Y10T 29/53204* (2015.01)

(56) References Cited

U.S. PATENT DOCUMENTS

| | | | | |
|---|---|---|---|---|
| 7,244,310 B2* | 7/2007 | Edwards | ............... | B41J 2/04505 118/669 |
| 7,361,500 B2* | 4/2008 | Stett | ................. | G01N 33/48728 435/285.2 |
| 7,384,733 B1* | 6/2008 | Byrne | ................... | C12M 41/46 204/403.01 |
| 7,749,416 B2* | 7/2010 | Ota | ........................ | B41J 2/1603 264/104 |
| 8,293,524 B2* | 10/2012 | Ionescu-Zanetti | ........................... | B01L 3/502738 435/287.1 |
| 2002/0098575 A1* | 7/2002 | Mathes | ............ | G01N 33/48721 435/287.3 |
| 2003/0138767 A1* | 7/2003 | Bullen | ............. | G01N 33/48728 435/4 |
| 2005/0255446 A1* | 11/2005 | Vasylyev | ......... | G01N 33/48728 435/4 |
| 2006/0024802 A1* | 2/2006 | Muller | .............. | B01L 3/502761 435/173.1 |
| 2007/0023960 A1* | 2/2007 | Ota | ........................ | B41J 2/1603 264/272.16 |
| 2008/0153146 A1* | 6/2008 | Stett | ................. | G01N 33/48728 435/173.4 |
| 2011/0045582 A1* | 2/2011 | Lee | ................... | B01L 3/502707 435/307.1 |
| 2013/0259715 A1* | 10/2013 | Hilt | ........................ | B60C 23/04 417/300 |

* cited by examiner

METHOD AND DEVICE FOR AUTOMATICALLY DETERMINING THE POSITION OF A MICROSYSTEM FOR MANIPULATING A SPHERICAL MICROOBJECT

CROSS-REFERENCE TO RELATED APPLICATIONS

This application is a continuation of U.S. Ser. No. 14/080,643, filed Nov. 14, 2013 and published as US 2014/0137396 A1, which is a continuation of International Patent Application No. PCT/EP2011/058122, filed May 19, 2011 and designating the United States and published as WO 2012/155973 A1. The entire contents of these prior applications are incorporated herein by reference for all purposes.

The present invention relates to a method for automated determination of the relative position between a first hole on a first microsystem component, which is preferably provided with a first channel opening in the first hole, and at least one second hole on a second microsystem component, which is preferably provided with a second channel opening in the second hole, wherein the two microsystem components are located in a liquid medium at least in the region of the holes.

The present invention furthermore relates to a device for the automated contacting of at least one microscopic test object, preferably a biological cell, wherein the test object is immobilized on a first hole and is then contacted through a second hole, comprising at least one first microsystem component, on which the first hole is provided and which is preferably provided with a first channel opening in the first hole, at least one second microsystem component, on which the second hole is provided and which is preferably provided with a second channel opening in the second hole, and comprising a reaction vessel for holding a liquid medium, the two microsystem components being immersed in the medium at least in the region of the holes.

In connection with the present invention, "contacting" is intended to mean both direct physical contact with the surface or the interior of the microscopic test object and the application of substances onto the surface or into the interior of this microscopic test object. Furthermore, the contacting according to the invention also includes the removal of substances from such a microscopic test object.

In the scope of the present invention, a "microscopic test object" is intended to mean a test object which is in suspension and has dimensions in the range of a few µm to several tens of µm, preferably from about 5 to about 50 µm. These test objects include individual cell culture cells, cell clusters, oocytes, polymer microspheres, empty cell envelopes, etc.

These microscopic test objects are generally sucked onto the first hole and temporarily held, i.e. immobilized, there by negative pressure. They are then contacted through the second hole, in order to be able to carry out measurements on the test object or in order to be able to manipulate the test object in the above sense.

In this context, a "microsystem component" is intended to mean a part which is suitable for immobilizing or contacting the microscopic test objects. Such parts may be formed as micro-cannulas or pipettes, and they may also comprise microsystem technology elements which can be positioned in the micrometer range.

"Microsystem technology" means miniaturized instruments, modules and parts whose components have very small dimensions in the micrometer range and which interact as a system.

The first hole, on which the microscopic test object is intended to be at least temporarily immobilized, may for example be a hole on a holding pipette or a membrane pore on a microsystem technology part. This hole may be connected to a channel extending in the first microsystem component, or it may be formed as a pure pore.

In order to be able to contact the test object immobilized on the first hole, the hole of a second microsystem component must be positioned in the micrometer range with respect to the first hole, or the test object. This second hole may be formed on a micro-cannula in which a measurement electrode is arranged, although the micro-cannula may also be formed as an injection cannula or as a suction cannula.

Owing to the production processes, however, in the microsystem components in question here the exact positions of the holes on the microsystem components are not known in many cases, at least not within the order of magnitude range of a few micrometers which is of interest here.

In view of the above, no rapid, economical and reliable methods are yet known with which two such microsystem components can be positioned with respect to one another in an automated fashion, in such a way that their holes are mutually aligned.

In the scope of the present invention, the term "mutually aligned" means that the two holes lie opposite one another in such a way that their middle axes extend through the other respective hole, and preferably coincide, and between the holes there is a distance which is no more than a few micrometers.

The previously available methods are all based on the position of the hole on the respective microsystem component either being determined beforehand by a user or being determined in the scope of an elaborate image recognition method.

When the position or location of the two holes with respect to one another is known, then the microsystem components can be positioned relative to one another in such a way that the holes are mutually aligned.

A method according to the invention and a device according to the invention are intended to be used in order to suck microscopic test objects which are in suspension onto the first hole and hold them there temporarily by negative pressure. The second microsystem component, which is generally formed as a micro-cannula, is then positioned in such a way that the second hole comes to lie on the surface or at a defined distance from the surface of the microscopic test object, or penetrates into the test object itself.

In this way, electrical measurements can be carried out on the surface or in the interior of the microscopic test object, it also being possible to introduce substances into the test object or suck them out of the test object.

When the second hole is arranged at a certain distance from the test object, the test objects may also be transiently stimulated, for example by directing special liquids for very short periods of time directly onto the surface of the test objects.

After the test object has been stimulated or excited in this way, another micro-cannula may be positioned against the test object in order to measure the effects of the stimulation.

Besides biological cells or synthetically produced microspheres, microcarriers or other solid bodies which lie in above-said diameter range may also be envisioned as test objects.

The device to be provided according to the invention and the method to be made available according to the invention are of particular interest for use in the field of the patch clamp technique, the development history and application possibilities of which are described for example in EP 0 980 523 B1, the content of which is hereby incorporated into the subject matter of the present application by reference.

In the conventionally used patch clamp technique, a single pipette is brought under microscopic observation onto the outside of an immobilized cell. To this end, the fragile glass pipette is placed by means of a micromanipulator under optical supervision by a skilled expert onto the cell membrane, which is then sucked onto the hole in the glass pipette by negative pressure.

Subsequently, measurements may optionally be carried out on the membrane patch, which is sealed against the surrounding liquid by means of the pipette and is electrically insulated by means of a so-called gigaseal. It is, however, also possible to open the membrane patch by a further pressure impulse so that there is direct contact with the interior of the cell.

Furthermore, it is also known to insert thinly drawn glass capillaries into a cell and then inject substances into the cell interior, or suck substances out of the cell interior.

Particularly in the methods which are based on drawn patch pipettes or injection pipettes, the exact site of the location of the hole on the pipette is not known.

The same applies for the position of micropores on surfaces, in which case the exact location of the micropore on the surface is often not known for reasons of production.

As already mentioned, however, for the use of the techniques provided according to the invention it is necessary to know the exact relative position between the two holes on two microsystem components, which are provided for immobilization and contacting of a microscopic test object.

In this context, already mentioned EP 0 980 523 B1 proposes to ascertain the position of a cell to be contacted and the position of the tip of a patch pipette in space in an automated fashion with the aid of an image processing system, and then to bring the tip in a controlled way onto the membrane surface of the cell to be contacted.

In other words, the search for a cell with which a patch clamp connection is intended to be established, and the determination of the location of the tip on the pipette, are based on optical information in digital images. The recognition method is carried out iteratively. After a first rough estimate of the position of the tip of the pipette and of the positioning of the pipette in the desired part of the image has been ascertained, the geometrical midline of the pipette is ascertained, with the aid of which the position of the hole of the channel in the pipette can then be deduced.

This method is not only extremely time consuming, but also requires very expensive and elaborate devices, which can furthermore be operated only by very well trained personnel.

For these reasons, the known method has not yet gained wide use.

From U.S. Pat. No. 7,384,733 B1, it is known to suck a cell, which is in suspension, onto the tip of a patch clamp pipette. To this end, a suspension of cells to be contacted is taken up in a glass capillary and then a patch clamp pipette is arranged centrally with respect to the hole of the glass capillary. The patch clamp pipette is subsequently moved stepwise toward the hole of the capillary and the resistance of the pipette relative to the surroundings is measured. With the aid of the resistance change, the time when the patch clamp pipette is immersed in the liquid, or contacts a cell which is then sucked on by negative pressure, is recognized.

In this method, it is on the one hand disadvantageous that the cells which are in suspension come in contact with the tip of the patch clamp pipette only by random encounter. In order to increase the probability, many cells are therefore taken into suspension, even if only one of these cells is intended to be contacted.

In this method, it is therefore on the one hand disadvantageous that a large number of cells have to be held in stock, even if only one cell is respectively intended to be contacted.

It is furthermore disadvantageous that the method can only be started when the tip of the patch clamp pipette has already been aligned by operating personnel coaxially with the capillary in which the cells are held in suspension. This type of alignment, however, is not sufficiently precise for many applications. Furthermore, the alignment depends on the experience of the operating personnel and is therefore also not sufficiently reliable and reproducible.

The known method only starts to work when the information which is to be provided for the first time according to the invention is already available, the quality and reproducibility of this information often not being sufficient in the prior art.

The method known from U.S. Pat. No. 7,384,733 B1 is thus not fully automatable, as the positioning of the patch clamp pipette with respect to the capillary must be carried out manually, which entails the disadvantages explained.

A similar method is described by US 2003/0138767 A1. After a pipette has been clamped in a holder and aligned with a vessel in which cells are held in suspension, the pipette is automatically moved toward the liquid present in the vessel.

The pipette is a patch clamp pipette which is operated in the current clamp mode, in which the current is kept constant and the developing voltage is measured.

When the pipette is immersed in the solution, this is recognized by a change in the measured voltage.

The patch clamp pipette is then changed to the voltage clamp mode, in order to measure the resistance in front of the pipette. With the aid of a resistance change, whether a cell has been sucked onto the tip of the pipette is then recognized.

An example of a glass pipette or glass capillary which can be used for patch clamp experiments may be found in WO 2007/107375 A2.

The problem of positioning a cell on a hole, on which it can then be contacted in an automated fashion in the sense of the patch clamp technique, is also addressed in WO 01/94939 A1 and EP 1 311 655 B1.

These methods are based on cells that are individualized in microchannel systems and then fed through channels and sucked onto lateral holes in these channels. The cells positioned in this way are then contacted by means of a patch clamp pipette arranged concentrically with the suction hole or are penetrated by means of suitable pipettes.

In these methods as well, the exact geometrical shape and arrangement of the patch clamp pipette are known before the method can begin at all.

A common feature of all the methods described so far is that one cell, which is subsequently measured, is selected purely at random from a large number of cells. In this case, in practice, it regularly happens that dead cells, cell debris or contaminants are sucked onto the patch clamp pipette, which leads to abortion of the experiment. Besides the time aspect, a further disadvantage in this case is that the patch clamp pipette cannot be used again but must be disposed of.

It would therefore be desirable if individual cells could be selected in a controlled way from a number of available cells and checked for their suitability for the planned measurement before the actual measurement. To this end, however, exact and reproducibly obtainable knowledge about the shape and position of the patch clamp pipette is necessary.

In view of this prior art, it is an object of the present invention to provide a method and a device of the type mentioned at the outset, which make it possible to position the two microsystem components with respect to one another in such a way that their holes are mutually aligned. The intention is in this case that the new method can be carried out rapidly and reliably even by less highly specialized personnel, and the new device is intended to be constructed simply and economically.

In the method mentioned t the outset, this object is achieved according to the invention by the steps:

under the supervision of a control device controlled by a computer, the first and second microsystem components are displaced relative to one another into different relative positions, electrical signals are delivered by one of the two microsystem components and are recorded on the other of the two microsystem components as measurement values which depend on the relative position of the two microsystem components with respect to one another, for different relative positions between the two microsystem components, measurement values are determined, from which in the control device the relative position is ascertained into which the two microsystem components are to be positioned with respect to one another in such a way that their holes are mutually aligned.

In the device mentioned at the outset, this object is achieved in that a mechanism is provided, by means of which the two microsystem components can be displaced relative to one another at least along two mutually orthogonal spatial axes, a control device is provided, by means of which the mechanism is controlled in an automated fashion, and a measurement arrangement is provided, by means of which electrical signals are delivered by one of the two microsystem components and are recorded on the other of the two microsystem components as measurement values which depend on the relative position of the two microsystem components with respect to one another, the control device being adapted in order to ascertain, from measurement values for different relative positions between the two microsystem components, the relative position in which the two microsystem components are to be positioned with respect to one another in such a way that their holes are mutually aligned.

The object of the present invention is fully achieved in this way.

The present invention therefore provides for the first time the basis of a simple and reliable automated method and an economical automated device with which microscopic test objects, preferably biological cells, can rapidly and reproducibly be immobilized and contacted in a controlled way.

Specifically, the inventors of the present application have recognized that, even in the micrometer range, it is possible to displace microsystem components into different relative positions with respect to one another and, for these respective positions, to record measurement values which are a measure of the relative position with respect to one another. If a relatively large number of such measurement values have been recorded, then it is possible to calculate in an automated fashion how the microsystem components need to be positioned with respect to one another so that their respective holes are mutually aligned, their respective midlines extend through the other respective hole, and the distance between the holes is only a few micrometers so that flat contact is just still avoided.

The new method and the new device in this case entirely obviate optical or image processing devices and measures, the intervention of operating individuals also not being necessary.

Rather, the two microsystem components merely need to be mounted on the mechanism and brought into the corresponding liquid medium, whereupon the "search method" can begin. The search strategy is in this case programmed in such a way that manual interventions are not necessary for either the conduct or the evaluation of the search method.

It could not have been expected that this method, based on the transmission of electrical signals, makes it possible to determine the relative position of microscopic holes in microsystem components with the necessary accuracy.

In this context, it should be recalled that the size of the holes in the microsystem components lies in the range of from <1 µm to at most 10 µm, so that it is possible to position test objects whose diameters preferably lie in the range of from 5 to 50 µm.

The geometrical shape of the microsystem components is furthermore not predetermined and reproducible; rather, in particular the drawn tips of glass capillaries are of different length and also different in their shape: they may be more or less bent or curved. It is furthermore conceivable for the holes not always to be arranged centrally on the microsystem components; rather, for reasons of manufacture, they lie very differently in the exit surface of the respective microsystem components.

This also applies for micropores on surfaces of microsystem components, but in particular for such holes which serve as an opening of a channel which is provided in the respective microsystem component.

Through these channels, in the case of a microsystem component provided for holding a test object, it is possible to apply negative pressures by which the test object is sucked onto the hole and then immobilized on the hole. Furthermore, a positive pressure may also be applied through this channel in order to remove the immobilized test object again from the hole.

If, on the other hand, the microsystem component is for example a pipette or cannula for contacting an immobilized test object, then an electrode may be provided in the channel in order to be able to carry out measurements on or in the test object. Furthermore, test substances may be delivered onto the test object or into the test object, or substances may be sucked out of the test object, through the channel.

Microsystem components, in particular patch clamp pipettes or glass capillaries, are provided for all these different functions, and for these the location of the hole on the tip can be determined accurately in relation to the location of the hole on the tip of the other microsystem component with the aid of the new device, or the new method, irrespective of their geometrical shape.

In other words, the result of the new search method is an indication of the relative position, between the two microsystem components, in which the holes are mutually aligned to the described extent. Since the exact position of the hole on the microsystem component itself is not known for the two microsystem components, the new method does not provide precise information about where the position of the hole is on the respective microsystem component; rather, it provides information about how the overall system consisting of the mechanism and the microsystem components is to be relatively positioned so that the holes are mutually aligned.

In this case, of course, it is not necessary to displace both microsystem components in space; it is entirely sufficient for one of the two microsystem components to be displaced.

In an improvement, it is then preferred for the electrical signals to be delivered into the medium by means of a signal electrode arranged in the first channel, and for the measurement values to be recorded by means of a measurement electrode accommodated in the second channel, the electrical signals preferably being voltage pulses delivered into the medium, the pulse amplitudes of which are acquired as measurement values at the second microsystem component.

Here, it is advantageous that a particularly simple but nevertheless particularly accurate way of determining the measurement values characterizing the relative position consists in delivering signals into the medium at the holes themselves, and respectively recording them from the medium, and further processing them as a measurement value.

With this measure, it is particularly surprising that simple voltage pulses can be used as electrical signals, their pulse amplitude being a measure of the relative position of the microsystem components, or more precisely of the holes on the microsystem components with respect to one another.

In this case, it is furthermore preferred for the two microsystem components to be displaced with respect to one another along at least two mutually orthogonal spatial axes, the first spatial axis extending approximately parallel to the projections of the longitudinal axes of the two holes into the plane spanned by the two spatial axes.

With this measure, it is advantageous that the search method is carried out relatively simply. First, the two microsystem components are displaced with respect to one another along the first spatial axis, the measurement values being taken for different positions along this spatial axis. Next, the microsystem components are displaced with respect to one another along the second spatial axis, in which case the measurement values are again taken for determined positions along the second spatial axis.

From the profile of the measurement values along the first and second spatial axes, it is then possible to determine the relative position for the two microsystem components, with respect to one another, in which the holes are mutually aligned.

The first spatial axis in this case extends approximately parallel to the projections of the longitudinal axes of the microsystem components into the plane which is spanned by the two spatial axes. This means none other than that the first spatial axis extends approximately parallel to the microsystem components, irrespective of whether the microsystem component itself lies in the plane spanned by the two spatial axes or "dips" into this plane obliquely from above. This oblique arrangement may be advantageous when the microsystem components are immersed laterally from above in the medium which is used to transport the electrical signals, but above all in order to record the test objects held in suspension.

This type of arrangement avoids the possibility of a collision taking place between the tips of the two microsystem components while the new method is being carried out. If the microsystem components are first displaced with respect to one another along the first spatial axis, then they run parallel next to one another, in which case, according to the inventors' experience, the measurement values already indicate the "height" at which the two holes approximately lie along the first spatial axis. The control system will then arrange the two microsystem components with respect to one another along the first spatial axis, in such a way that there is a safety distance between the holes in the direction of the first spatial axis. In this position, the system will then displace the two microsystem components with respect to one another along the second spatial axis, and a collision cannot then occur in this case because the safety distance has been set up between the tips.

In this case, it is preferred that a rough relative position is determined along the first spatial axis by displacing the two microsystem components along the first spatial axis into different relative positions while maintaining a constant fixed relative position along the second spatial axis and determining a measurement value for each relative position, a rough relative position preferably being determined along the second spatial axis by displacing the two microsystem components along the second spatial axis into different relative positions while maintaining a constant fixed relative position along the first spatial axis and taking a measurement value for each relative position.

The fixed relative position along the second spatial axis is in this case selected in such a way that there is a safety distance, which is determined as a function of the dimensions of the microsystem components in the direction of the second spatial axis, between the two microsystem components in the direction of the second spatial axis. Preferably, the fixed relative position along the first spatial axis is then selected in such a way that there is a safety distance, which is determined as a function of the previously determined, rough relative position along the first spatial axis, between the two holes in the direction of the first spatial axis.

Neither the initial adjustment nor the conduct of this method requires input by operating personnel, since, in the initial setting, the mechanism is automatically adjusted in such a way that, with a clamped first microsystem component and a clamped second microsystem component, these have a relative starting position in the direction of the second spatial axis which ensures a sufficient safety distance. As a function of the type of microsystem components, or as a function of their dimensions, this safety distance is in this case either calculated by an algorithm or taken from a corresponding table.

For the case in which the new device and the new method are always used in a special laboratory situation with special holding pipettes and patch clamp pipettes of known macroscopic geometrical dimensions, the same starting position with a corresponding safety distance may also be used in each case.

The method steps described so far then lead to a relative roughly resolved position, in which the holes are already roughly aligned with one another, being determined both along the first spatial axis and along the second spatial axis.

In order now to refine this alignment, that is to say in order to mutually align the holes even more accurately, a finely resolved relative position is determined along the first spatial axis by displacing the two microsystem components along the first spatial axis into different relative positions while maintaining a constant rough relative position along the second spatial axis and taking a measurement value for each relative position, a finely resolved relative position furthermore preferably being determined along the second spatial axis by displacing the two microsystem components along the second spatial axis into different relative positions while maintaining a constant, finely resolved relative position along the first spatial axis and taking a measurement value for each relative position.

These steps for determining the finely resolved relative position are therefore a repeat of the steps which led to the roughly resolved relative position, the starting positions along the first and second spatial axes now respectively being determined from the relative position which was determined in the respectively preceding method step for the other respective axis.

In other words, the method starts from a safety distance along the second spatial axis and determines the rough relative position along the first spatial axis. On the basis of this rough relative position along the first spatial axis, a rough relative position along the second spatial axis is then determined. On the basis of this relative rough position along the second spatial axis, a finely resolved relative position along the first spatial axis is then determined, which is then in turn the starting point for the determination of the finely resolved relative position along the second spatial axis.

These method steps may be repeated several times in succession, so as finally to reach a relative position between the two microsystem components along the first and second spatial axes, in which the two holes are mutually aligned with sufficient accuracy.

The method steps may, for example, be iteratively repeated several times until no further improvements in the relative positions are achieved, or until the improvements lie in the micrometer range.

Of course, it is also possible in precisely the same way to determine the relative position of the two microsystem components with respect to one another along a third spatial axis, which is orthogonal to the first and second spatial axes. The starting point for carrying out the method along the third spatial axis may in this case be either a safety position, a rough relative position or a finely resolved relative position.

In this case, it is preferred for the two microsystem components to be displaced relative to one another along a third spatial axis which extends orthogonally to the first and second spatial axes, a relative position being determined in the third spatial axis by displacing the two microsystem components along the third spatial axis into different relative positions while maintaining a fixed relative position along the first and second spatial axes and taking a measurement value for each relative position.

In general, it is also preferred for the first microsystem component to be configured for immobilizing a biological cell and for the second microsystem component to be configured for contacting the cell immobilized in this way.

With this measure, it is advantageous that the new method and the new device can then be used in conjunction with examinations according to the patch clamp technique or for injection of substances into the cell, or for extracting substances from the cell.

Accordingly, the present invention also relates to a method for the automated contacting of at least one microscopic test object which is immobilized at a hole of a first microsystem component and is then contacted through a hole on a second microsystem component, wherein
  the relative position between the two holes is determined with the new method, then
  a test object is immobilized on the first hole, then
  the test object is preferably checked for its suitability for subsequent examinations, then
  the two holes are mutually aligned along a first spatial direction with a distance which corresponds to at least two times the maximum diameter of the test object to be contacted, then
  the resistance in front of the second hole is measured by means of a sensor electrode, and then
  in a search method, the distance between the two holes in the first direction is reduced stepwise and the resistance is measured again for each new distance,
  the search method being ended, and the test object being evaluated as contacted, when there is a predetermined change in the measured resistance value.

This method extends far beyond the method as is known from documents U.S. Pat. No. 7,384,733 B1 and US 2003/0138767 A1, discussed at the outset, because now according to the invention the position of the holes with respect to one another is determined with the new method or the new device.

As soon as this relative position is known, the two microsystem components may be displaced relative to one another in such a way that their holes are at a determined distance from one another along the first spatial axis, but are mutually aligned along the second spatial axis and optionally the third spatial axis.

This distance between the two holes along the first spatial axis is in this case selected in such a way that it is significantly greater than the diameter of a test object to be immobilized.

The vicinity of the two microsystem components is then flushed with a solution in which test objects are in suspension. A small negative pressure is in this case applied to the hole of the first microsystem component, the effect of which is that test objects diffusing past are sucked onto the first hole. On the basis of a change in the negative pressure or a change in the electric field at or in front of the first hole, the fact that a cell has been sucked and immobilized is in this case recognized.

Subsequently, according to the described method, the second microsystem component is then moved stepwise toward the first microsystem component while the resistance is measured continuously in the voltage clamp mode and/or the current clamp mode. On the basis of a change in the resistance, it is then possible to recognize that the second hole has touched the membrane of the test object.

From the relative positions of the microsystem components with respect to one another when the holes lie immediately in front of one another, on the one hand, and when there is an immobilized test object on the other hand, it is now possible to determine the diameter of the test object, which corresponds to the difference between the relative positions in the direction of the first spatial axis.

Information about the diameter of the test object can now be used, on the one hand, in order to check whether a desired test object has actually been immobilized. In this way, for example, it is possible to establish whether cell debris or defective test objects have been immobilized, or whether a test object suitable for the rest of the method has been "captured".

This assessment of the suitability of the "captured" test object for the planned examinations may also be carried out by examining the test object immobilized on the first hole optically, electrically or by other suitable methods. In this way, from a large number of cells, which may possibly contain only a few cells which are actually suitable for the planned examination, one of the suitable cells can be found in a controlled way. If the immobilized test object is unsuitable, it is discarded and a new cell is sucked on.

Therefore, although with the new method it is not possible to pick out only a suitable cell directly from the suspension in a controlled way, the randomly immobilized cells can nevertheless be examined for their suitability before the actual examination method begins. It is therefore not necessary to increase the proportion of suitable cells in the suspension by other methods before the actual measurement, which is furthermore not always possible.

Subsequently, the second microsystem component may for example be inserted into the immobilized and qualified test object, if it is a glass cannula through which substances can be introduced into the test object or extracted from the test object. On the other hand, the second hole may be applied onto the surface of the test object in such a way as to form a so-called gigaseal, so that measurements can be carried out either on the enclosing membrane patch or, after corresponding perforation of the membrane patch, on the entire test object.

It is particularly advantageous in this case that holding of the test object is carried out not by the patch clamp pipette but by the first hole, which may for example be formed on a holding pipette. During the immobilization of the cell, this prevents liquid from being sucked into the patch clamp pipette and being mixed there with the liquid in the patch clamp pipette.

Specifically, this liquid in the patch clamp pipette differs for biological and metrological reasons from the liquid in which the cells are in suspension, so that in the prior art it is necessary by elaborate measures to prevent this mixing from having a detrimental effect.

Since, according to the invention, the two holes can now for the first time be automatically positioned with respect to one another with high accuracy, the patch clamp pipette can be relieved of the suction task because it can be positioned on the first hole, accurately on the surface of the cell, after the immobilization and optionally qualification of the cell.

Furthermore, it is possible to deliver test substances in a controlled way onto the surface of an immobilized test object through the second microsystem component, the distance between the surface of the test object and the second hole being selectable in any desired way, but with sufficient accuracy, with the aid of the information determined by the method according to the invention.

In this case, it is preferred for the resistance in front of the first hole to be measured by means of a sensor electrode during the immobilization of the test object on the first hole. This method is carried out in the same way as the previously described recognition of the contact of the already immobilized test object on the second hole.

Furthermore, it is possible to move the test object, immobilized on the first hole and successfully contacted by the described method, away from the first microsystem component with the aid of the second microsystem component, by displacing the two microsystem components relative to one another.

To this end, either the natural adhesion of the test object on the second microsystem component or a slight negative pressure applied to the second microsystem component may be used in order to hold the test object on the second microsystem component.

In this way, it is possible to bring the test object to a different location. In particular, it is possible to position the test object with the aid of the second microsystem component at a suitable distance relative to the hole of the first microsystem component, and then to deliver test substances onto the surface of an immobilized test object in a controlled way through the first microsystem component. The distance between the surface of the test object and the hole may in this case be selected in any desired way, but with sufficient accuracy, with the aid of the information determined by the method according to the invention.

This is advantageous in particular because in this configuration, a measurement can simultaneously be carried out on the test object with the second microsystem component, while a test substance is delivered onto the test object by the first microsystem component.

In a variant of the method described above, a further third microsystem component is used in order to deliver test substances onto the surface of the test object. This third microsystem component may be connected in a mechanically fixed way to the first microsystem component, so that the information determined by the method according to the invention about the location of the hole on the first microsystem component also constitutes sufficient information about the location of the hole on the third microsystem component.

This information may either be derived from the structure or determined once by the method according to the invention with the aid of a second hole. In this way, the relative position between the first and second holes and between the second and third holes is determined once in the manner according to the invention at the start of a series of measurements, and the invariant relative position between the first and third holes is determined from this information and used for the further measurements.

While the first and third microsystem components are not replaced during the series of measurements, the second microsystem component, which may be a patch clamp pipette, may be replaced.

After this replacement, it is merely necessary to redetermine the relative position between the new second hole and the previous first hole, whereupon the relative position between the new second hole and the previous third hole can be determined from the previous measurements.

On the other hand, the relative position between the first and second holes, and then the relative position between the second hole and a third hole on a third microsystem component, may also initially be determined each time in the method according to the invention.

In general, the present invention also relates to a device which is adapted for carrying out the new method.

Further advantages may be found in the description and the appended drawing.

It is to be understood that the features mentioned above and those yet to be explained below may be used not only in the combination respectively indicated, but also in other combinations or individually, without departing from the scope of the present invention.

Embodiments of the invention are represented in the appended drawing and will be explained in more detail in the description below.

Figure 1:
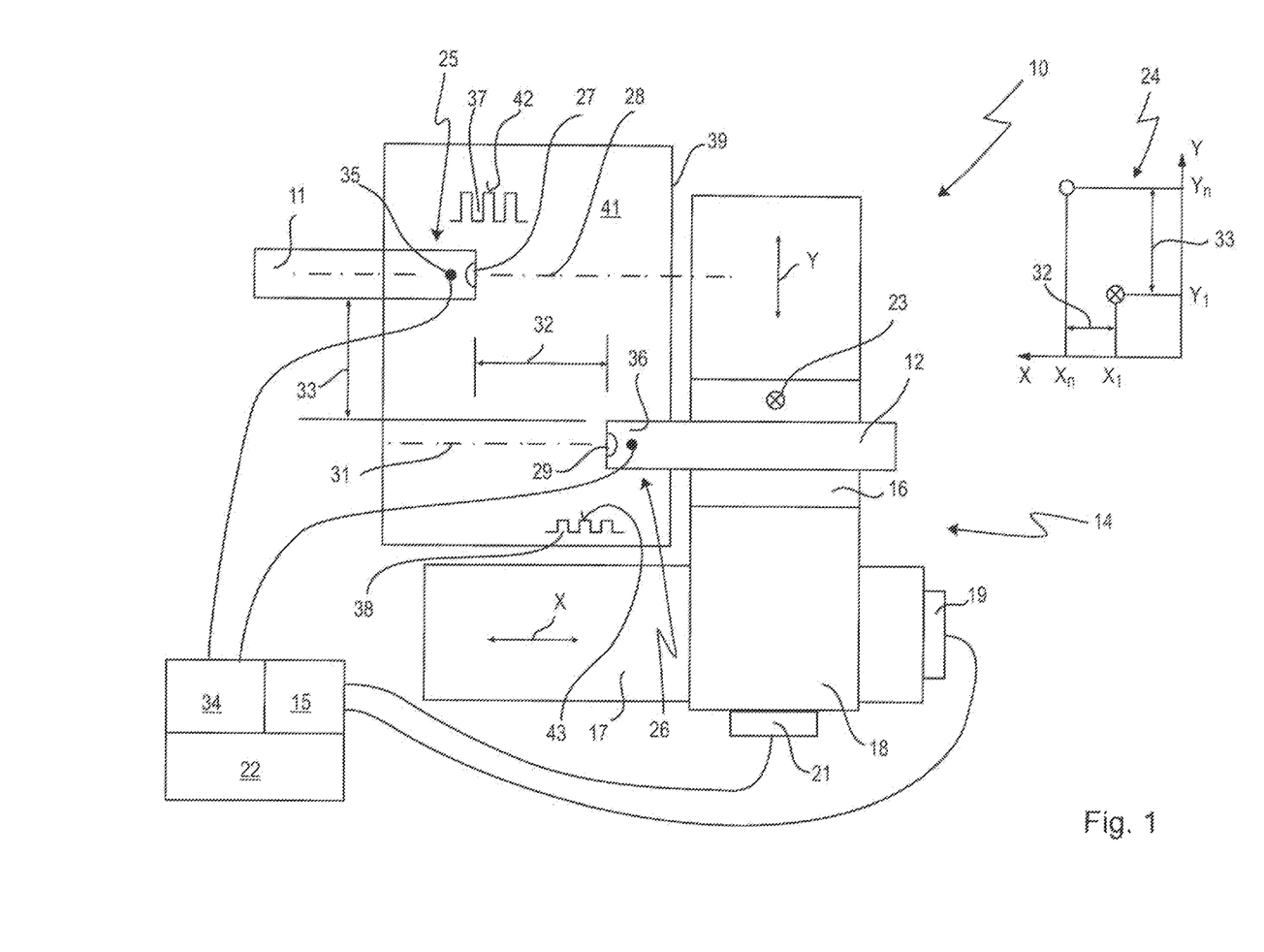
FIG. 1 shows a schematic plan view of the new device in its basic position.

In FIG. 1, a device for automated determination of the relative position between two microsystem components 11 and 12 is schematically shown by 10.

The device 10 comprises a mechanism 14, by means of which the two microsystem components 11 and 12 can be displaced relative to one another under the supervision of a computer-controlled control device 15 in the two orthogonal spatial axes x and y.

To this end, the mechanism 14 comprises a carriage 16, on which the second microsystem component 12 is fastened. The first microsystem component 11 is arranged spatially fixed.

The mechanism 14 furthermore comprises an x guide 17, on which a y guide 18 which can be displaced in the x direction, and on which the carriage 16 is mounted displaceably in the y direction, is arranged.

The y guide is displaced by means of an x motor 19 in the x direction, and the carriage 16 is displaced by means of a y motor 21 in the y direction.

The movements of the carriage 16 take place under the supervision of a computer 22, into which the control device 15 may be integrated.

A reference point 23, the position or location of which is predetermined by the computer 22 in a coordinate system indicated at 24, is indicated by way of example on the carriage 16.

In the basic position shown in FIG. 1, the carriage 16, i.e. the reference point 23, lies at the position x1/y1, which is indicated in the coordinate system 24.

The two microsystem components 11 and 12 shall now be displaced relative to one another in such a way that their tips 25 and 26 are mutually aligned. More precisely, this involves mutually aligning a hole 27 having a longitudinal axis 28 on the first microsystem component 11 with a hole 29 having a longitudinal axis 31 on the second microsystem component 12, in such a way that they lie directly in front of one another so that the tips 25 and 26 almost touch with their end sides and the longitudinal axis 28 lies in the hole 29, while the longitudinal axis 31 lies in the hole 27. Preferably, the longitudinal axes 28 and 31 are to coincide when the holes 27 and 29 are mutually aligned according to the invention.

In order to achieve this alignment of the holes 27 and 29, the microsystem component 12 must be displaced in the x direction by an actuation distance 32 and in the y direction by an actuation distance 33, as is indicated in FIG. 1 both on the device 10 and in the coordinate system 24.

A problem in this case is now that the exact position of the tip 25, or of the hole 27, is just as poorly known as the exact position of the hole 29 with respect to the reference point 23.

This uncertainty is due to the variations, for reasons of production, in the length of the tips 25 and 26 as well as in the location of the holes 27 and 29 on the tips 25 and 26.

The actuation distances 32 and 33 are therefore unknown, and first need to be ascertained so that the microsystem component 12 can be displaced into a relative position, with respect to the microsystem component 11, in which the holes 27 and 29 are mutually aligned.

According to the invention, therefore, a measurement arrangement 34 is provided in the computer 22, which arrangement interacts with a signal electrode 35 at the hole 27 in the first microsystem component 11 and with a measurement electrode 36 at the hole 29 in the microsystem component 12.

By means of the measurement arrangement 34, a chronological sequence of voltage pulses 37 is output at the signal electrode 35, which are measured as a chronological sequence of measurement values 38 at the measurement electrode 36.

Figure 2:
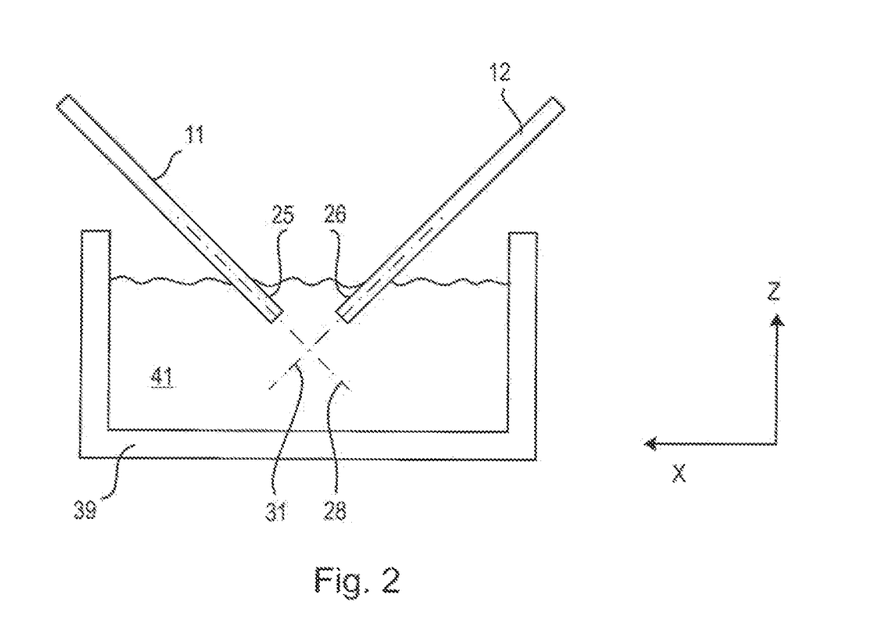
FIG. 2 shows a front view of the reaction vessel which is fitted in the device of FIG. 1 and into which two microsystem components are immersed with their tips.

So that this measurement is possible, the tips 25 and 26 of the microsystem components 11 and 12 are immersed in a reaction vessel 39 which is filled with a liquid medium 41, as can be seen particularly in the side view of FIG. 2.

The reaction vessel 39 and the medium 41 are also required in order to guide test objects to the microsystem components 11, 12 and to carry out measurements or manipulations on these test objects, as will be described in more detail below.

It can be seen from FIG. 2 that the microsystem components 11 and 12 are arranged with their longitudinal axes 28 and 31 inclined in the x/z plane, i.e. they point with their tips 25 and 26 obliquely from above, i.e. as seen in the z direction, into the medium 41.

The arrangement is in this case organized in such a way that the projection of the longitudinal axes 28 and 31 in the x/y plane, as shown in FIG. 1, extends parallel to the y axis and transversely with respect to the y axis.

Returning to FIG. 1, it can be seen that the voltage pulses 37 have a pulse amplitude 42 which has a higher value than the pulse amplitudes 43 of the measurement values 38 that are acquired at the measurement electrode 36 and are forwarded to the measurement arrangement 34.

The difference in the pulse amplitudes 42 and 43 is a measure of the distance between the holes 27 and 29. This difference is now used according to the invention in order to ascertain both the actuation distance 32 and the actuation distance 33 in a search method, as will now be explained with the aid of FIG. 3.

Figure 3:
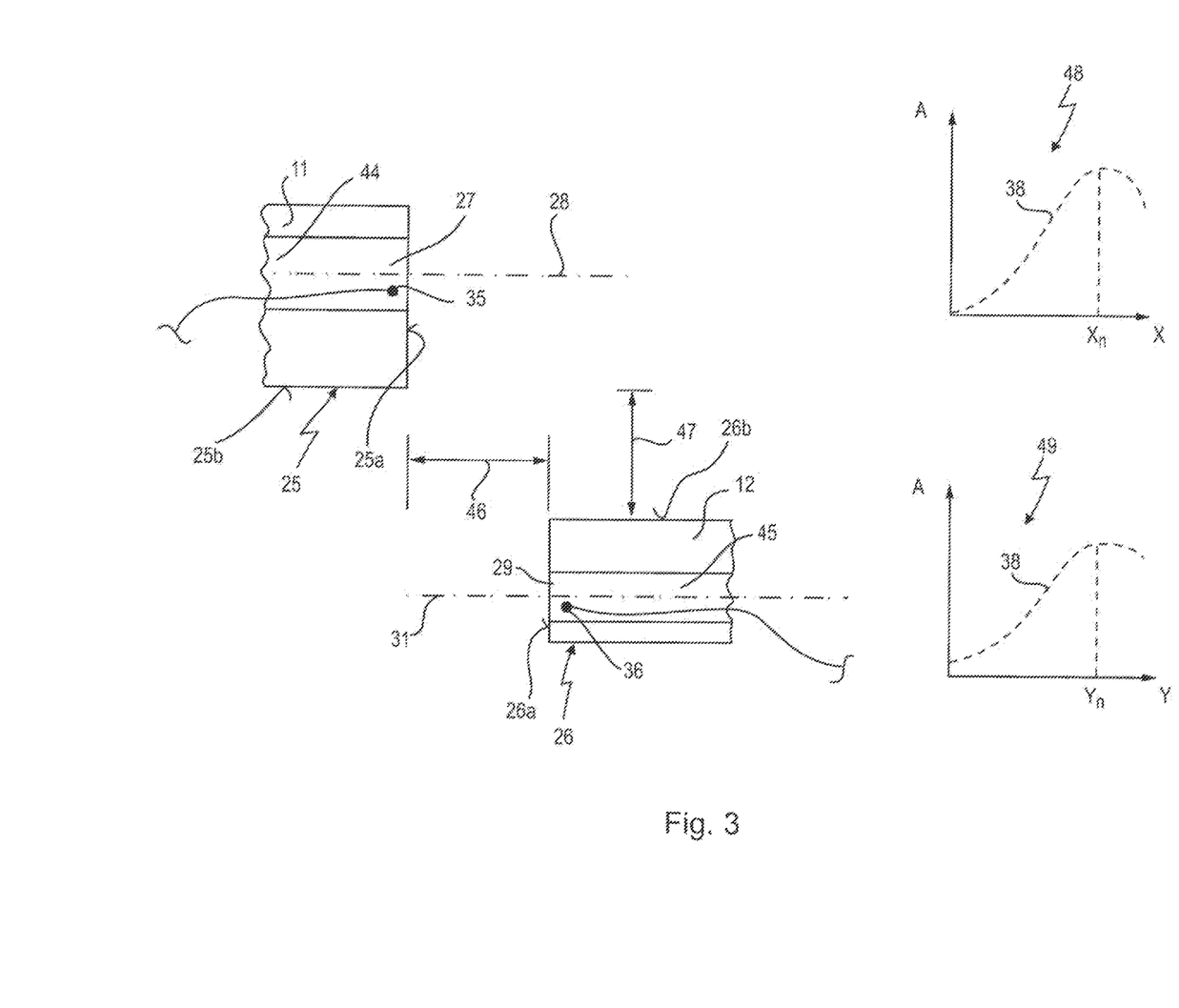
FIG. 3 shows the tips of two microsystem components in a schematic plan view and diagrams of measurement values for different relative positions of the microsystem components with respect to one another.

In FIG. 3, two microsystem components 11 and 12 are firstly shown in the region of their tips 25 and 26, respectively, on which the holes 27 and 29 are provided. These holes 27 and 29 are openings of channels 44 and 45, respectively, which extend in the microsystem components 11 and 12 and open on the end sides 25a and 26a, respectively, of the tips 25 and 26.

The first channel 44 in the microsystem component 11 is, for example, configured in order to suck a test object onto the hole 27 and hold it by negative pressure, or eject it again by positive pressure.

The second channel 45 is, for example, configured in order to carry out electrical measurements on the membrane of a test object, or from the interior of a test object, with the aid of the measurement electrode 36. The tip 26 may also be configured as a cannula, so that substances can be delivered onto a test object or into a test object, or substances can be sucked out of a test object, through the second channel 45, as will be explained in more detail below.

The relative positioning of the microsystem components 11 and 12 with respect to one another corresponds to the starting situation as shown in FIG. 1. As represented in FIGS. 1 and 3, the first microsystem component 11 and the second microsystem component 12 are mounted in the device 10, the carriage 16 being in the starting position in which the reference point 23 occupies the relative position x1/y1, as shown in the coordinate system 24 in FIG. 1.

With this arrangement, the end sides 25a and 26a have a safety distance 46 between them as seen in the x direction, while the tips 25 and 26 have a safety distance 47 from one another with their longitudinal sides 25b and 26b in the y direction.

These safety distances 46 and 47 are selected as a function of the macroscopic geometrical dimensions of the microsystem components 11 and 12 being used, in such a way that there is no risk of collision when the microsystem component 12 is displaced starting from the basic position shown in FIG. 3 either only in the x direction or else only in the y direction.

The search algorithm now proceeds in such a way that it initially displaces the microsystem component 12 stepwise in the x direction, measurement values 38 being taken for each relative position in the x direction (i.e. with a constant fixed position in the y direction).

FIG. 3 shows a diagram 48 which represents the pulse amplitudes A of the measurement values 38 for different x values.

For this given safety distance 47 in the y direction, there is a maximum of the measurement values 38 at the coordinate xn.

The microsystem component 12 is now displaced into the starting position of FIG. 3 or into the proximity of the roughly estimated relative position xm for the x direction, and is then correspondingly moved stepwise in the y direction, in which case again a measurement value 38 is taken for each relative position with a constantly fixed relative position in the x direction.

The profile of the pulse amplitudes A for different y values is represented in the diagram 49. At yn, the measurement values 38 have a maximum.

From these two diagrams, it can now be seen that the holes 27 and 29 are at least roughly aligned with one another when the microsystem component 12 is displaced into the relative position xn/yn.

Starting from the rough values xn/yn, the search method described above can be repeated, the safety distances 46 and 47 being reduced each time, but the microsystem component 12 not being displaced as far as the relative position xm/ym.

In this way, the relative position xm/ym of the second microsystem component 12 with respect to the first microsystem component 11 is iteratively refined in such a way that the holes 27 and 29 are increasingly more accurately aligned with one another when the microsystem component 12 is actually displaced into the relative position xn/yn.

Figure 4:
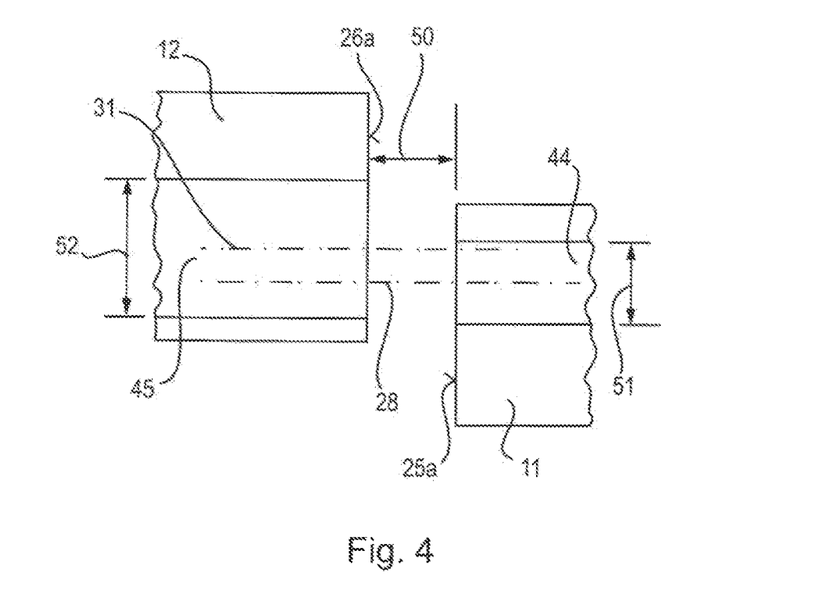
FIG. 4 shows two microsystem components, the holes of which are mutually aligned, in a representation as in FIG. 3.

This alignment of the two holes 27 and 29 with respect to one another is represented in FIG. 4.

In FIG. 4, it can firstly be seen that neither the hole 27 nor the hole 29 lies centrally in the end side 25a or 25b, respectively, so that in the case of mutually aligned holes 27 and 29 the tips 25 and 26 may be arranged offset with respect to one another.

In the alignment shown in FIG. 4, the holes 27 and 29 are mutually aligned in the sense of the present application since the midaxis 28 of the hole 27 extends in the hole 29, and the midaxis 31 of the hole 29 extends in the hole 27. In the ideal case, the midaxes 29 and 31 coincide exactly with one another when the holes 27 and 29 have been mutually aligned, that is to say when the second microsystem component 12 has been displaced into the relative position xn/yn, determined by the iteration method, with respect to the first microsystem component 11.

It should also be mentioned here that the distance of the end sides 25a and 25b from one another lies in the micrometer distance, and merely a residual safety distance 50 which prevents contact of the end sides 25a and 26a remains.

The channel 44 of the first microsystem component 11 moreover has a diameter 51 which lies in the range of from 3 to 5 μm, while the channel 45 in the second microsystem component 12 has a diameter 52 which is less than 1 μm.

The positioning method has been described so far only for the x/y plane, although a comparable iteration method is also carried out in order to align the holes 27 and 29 with respect to one another in the direction of the z spatial axis.

The method correspondingly proceeds in such a way that the two microsystem components 11 and 12 are arranged at a safety distance from one another in the x and/or y direction, whereupon the microsystem component 11 is then displaced along the z axis past the microsystem component 11 and a diagram corresponding to the diagrams 48 and 49 is recorded for the measured pulse amplitudes.

In this way, the position zn in which the holes 27 and 29 are mutually aligned in the direction of the z spatial axis is also determined.

After the method described above with the aid of FIGS. 1 to 4 has been carried out, a relative position xn/yn/zn in which the holes 27 and 29 are mutually aligned as shown with the aid of FIGS. 1 to 4 is stored in the computer 22.

Figure 5:
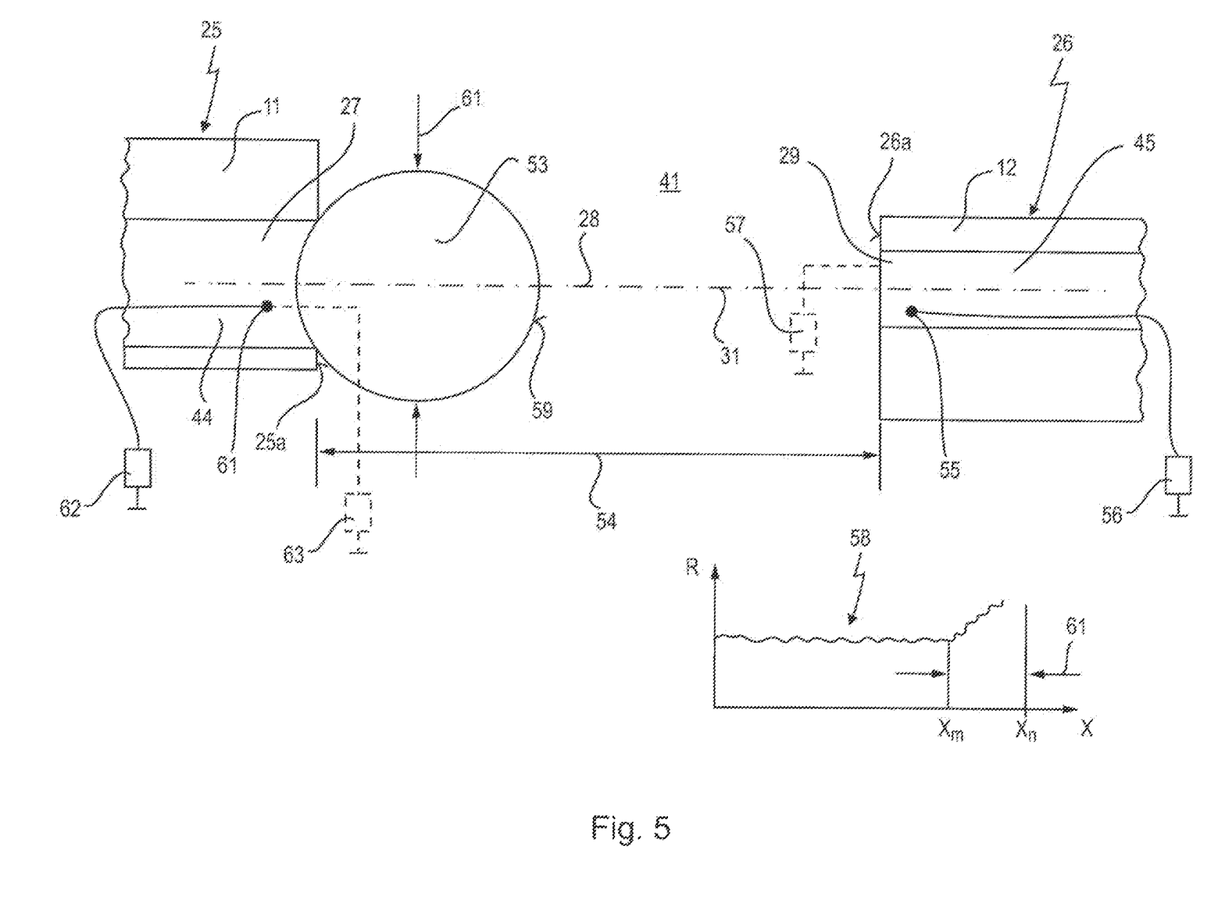
FIG. 5 shows two microsystem components, on one of which a microscopic test object is immobilized, in a representation as in FIG. 3, a diagram of the determination of the diameter of the test object furthermore being shown.

The device 10 is now ready for use, in order to immobilize a test object 53 on the microsystem component 11 and then contact it with the microsystem component 12, as will now be explained with the aid of FIG. 5.

To this end, test objects 53 suspended in the medium 41 are introduced into the reaction vessel 39. In the first channel 44, a negative pressure is then generated so that test objects 53 diffusing past the first hole 27 are sucked onto the hole 27 and immobilized, i.e. held, there by negative pressure. If the test objects 53 are intended to be released again, then a positive pressure is generated in the channel 44.

The fact that a test object 53 has been positioned on the hole 27 is recognized by the computer 22, for example by the fact that the negative pressure in the channel 44 increases.

The second microsystem component 12 has now been aligned with the first microsystem component 11 in such a way that the midaxes 28 and 31 coincide, or deviate from one another so slightly that they pass through the other respective hole. In the direction of the x spatial axis, a distance 54 which is at least two times the usual diameter of an object of the same type as the test object 53 is provided between the end sides 25a and 26a.

As already described, the test object is a microscopic test object whose usual diameter lies between 5 and 50 μm. The test object 53 may, for example, be a biological cell which is now contacted according to the patch clamp method.

In order now to be able to position the tip 26 of the second microsystem component 12 on the test object 53, or inside the test object 53, the diameter of the test object 53 must first be determined.

To this end, a sensor electrode 55 is arranged in the channel 45 at the hole 29 in the second microsystem component 12 and is connected to a circuit 56 which may in turn be integrated in the computer 22.

By means of the circuit 56, the sensor electrode 55 can be operated in a manner known per se in the voltage clamp mode or in the current clamp mode, so that the resistance indicated at 57 in front of the microsystem component 12 can be calculated with the aid of the varying voltage or the varying current, respectively.

When the end side 26a now approaches the test object 53, the resistance 57 initially remains constant, and the resistance value does not change until immediately before contact with the test object 53, for example increasing as shown in the diagram 58.

The relative x position of the microsystem component 12 is in this case at xm. In this relative position, the end side 26a is still separated from the end side 25a by the difference xn−xm, this difference thus corresponding to the diameter of the test object 53.

After the diameter of the test object 53 has now been ascertained, the computer 22 may initially check whether an appropriate test object 53 has actually been immobilized, or whether it is cell debris or excessively large or small particles which have been "picked out" from the medium 41.

If the test object 53 is not suitable, it is released back into the medium 41 by positive pressure in the channel 44, and the next test object 53 is sucked on by negative pressure in the channel 44.

If it is a suitable test object 53, however, the test object 53 may now be contacted on its membrane 59 by means of the second microsystem component 12.

All the information required so that the tip 26 can be pressed with its end side 26a onto the membrane 59 is stored in the computer 22.

The supervision of the immobilization of the test object 53 on the hole 27 may also be carried out with the aid of a sensor electrode 61 which is arranged in the first channel 44 of the first microsystem component 1 and is connected to a circuit 62, which may in turn be integrated in the computer 22.

By means of the circuit 62, the sensor electrode 61 can be operated in a manner known per se in the voltage clamp mode or in the current clamp mode, so that the resistance indicated at 63 in front of the microsystem component 11 can be calculated with the aid of the varying voltage or the varying current, respectively.

The time profile of the resistance value of the resistance 63 corresponds to the profile according to diagram 58, except that the time rather than the measured distance is now plotted on the x axis.

After the test object 53 has been recognized as immobilized, the diameter of the test object 53 can then be determined in the described way, and from this it can initially be ascertained whether it is a suitable test object 53.

Alternatively, however, the immobilized test object 53 may also be checked for its suitability for subsequent examinations by other methods, for example in an optical or electrical way.

When the test object 53 has been qualified as suitable, the method is continued, otherwise it is discarded and a new test object is sucked on and checked for suitability.

Depending on whether a measurement is then intended to be carried out on the membrane patch enclosed by the tip 26, or whether measurements are intended to be carried out on the entire cell, the membrane 59 is now perforated in the region of the hole 29 by applying a negative pressure in the channel 45, or the measurements which are carried out by means of the sensor electrode 55 are immediately started.

Likewise, it is now possible to insert the tip 26 partially into the test object 53 so as to introduce substances into the test object 53 or suck substances out of the test object 53.

Furthermore, it is possible to arrange the microsystem component 12 with a predetermined distance between the membrane 59 of the test object 53 and the end side 26a of the tip 26, in order then to deliver substances, which are intended to influence the behavior of the test object 53, onto the membrane 59 in pulses.

Furthermore, after the production of a gigaseal, it is possible to introduce test substances into the medium 51 in order to measure the reaction of the test object 53 to the test substances.

For these measurements, the sensor electrode 55 which is identical to the measurement electrode 36 is used. Likewise, the sensor electrode 61 is identical to the signal electrode 35.

After/before or during this measurement, the test object 53 may be transferred onto the second hole 29 and moved away from the first hole 27. By virtue of the known relative geometrical conditions, the test object 53 can be positioned at a defined distance from the first hole 27, from which test substances are then delivered onto the test object 53. With the electrode 36/55, the reactions of the test object 53 to these test substances can then be measured.

Of course, it is also possible to use not just one second microsystem component 12 but a plurality of microsystem components 12, for the holes of which the relative position with respect to the hole in the first microsystem component 11 is respectively determined.

In this case, it is also possible to arrange the microsystem component provided for holding the test object 53 on the carriage 16 and to arrange a plurality of microsystem components in the reaction vessel 39, which are used for contacting in the patch clamp mode and for flushing with test substances.

In such a case, for the microsystem component arranged on the carriage 16, in each individual case it is initially necessary to determine the relative position in which the hole of this microsystem component is aligned with each of the holes of the other microsystem components. The diameter of a captured test object, however, only needs to be determined once, and it can then respectively be taken into account when approaching the other microsystem components since the diameter is determined absolutely, in contrast to the relative positions of the various holes with respect to one another.

In this way, the device according to the invention provides the possibility of carrying out the method according to the invention, and therefore of successively carrying out measurements and/or manipulations on different test objects in an entirely automated way.

The precise determination of the relative positions of the individual microsystem components with respect to one another, into which they need to be brought so that the corresponding manipulations and/or measurements can be carried out, is then respectively carried out again and in an automated way when new microsystem components 11, 12 have been mounted in the device 10.

Figure 6:
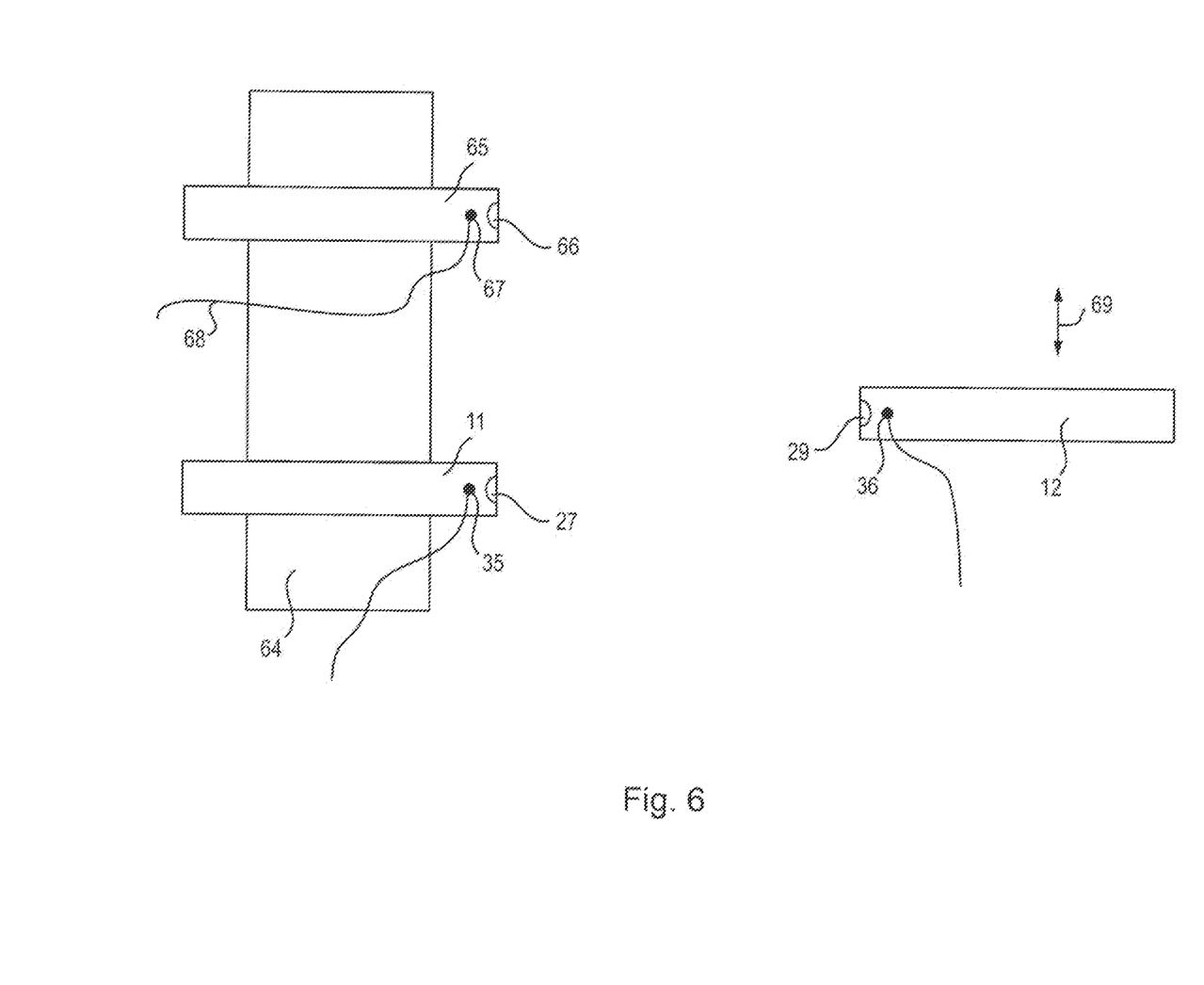
FIG. 6 shows a variant of the device shown in FIG. 1.

Furthermore, a third microsystem component 65 having a third hole 66 may be connected in a mechanically fixed way to the first microsystem component 11 on a carrier 64, as schematically shown in FIG. 6.

An electrode 67, which is connected via a cable 68 to the computer 22 of FIG. 1, is arranged in the hole 66. The electrode 67 may be used like the signal electrode 35 and/or like the sensor electrode 61, in order to determine the relative position between the hole 66 and the hole 29 in the described way, and/or in order to recognize whether a test object has been immobilized on the hole 66.

The second microsystem component 12 can be displaced relative to the two other microsystem components 11, 65, which is indicated by an arrow 69. In this way, a test object immobilized on the first hole 27 can be taken and transported to the third microsystem component 65, where test substances can then be delivered onto the test object from the third hole 66. With the electrode 36/55, the reactions of the test object to the test substances are then recorded.

In all these applications, the first microsystem component 11 is used in order to be able to immobilize a test object from a suspension and check whether it is suitable for the planned examinations. If the test object is qualified as suitable, then it can be contacted by the microsystem component 12 and optionally moved away from the first microsystem component 11. Test substances may then be delivered onto the test object from the first and/or a third microsystem component 11, 65.

In this way, from a suspension containing only a few suitable test objects, it is possible rapidly to find a suitable test object in a reproducible and reliable way and then subject it to the measurements.

These methods are only possible because, according to the new method, the relative positions of the holes 27, 29 and 66 with respect to one another can be determined automatically and with high accuracy.

The invention claimed is:

1. A method for automated determination of the relative position between a first hole on a first microsystem component and at least one second hole on a second microsystem component, wherein the two microsystem components are located in a liquid medium at least in the region of the holes, the method comprising:
   displacing the first and second microsystem components relative to one another into different relative positions, under supervision of a control device controlled by a computer,
   delivering electrical signals by one of the two microsystem components;
   recording the electrical signals on the other of the two microsystem components, measurement values of which depend on relative position of the two microsystem components with respect to one another,
   determining measurement values for different relative positions between the two microsystem components, and
   with the control device, determining from the measurement values a relative position into which the two microsystem components are positioned so that the first and second holes are mutually aligned.

2. The method of claim 1, wherein said first microsystem component is provided with a first channel opening in said first hole and said second microsystem component is provided with a second channel opening in said second hole.

3. The method of claim 2, wherein the electrical signals are delivered into the medium by a signal electrode arranged in the first channel, and the measurement values are recorded by a measurement electrode arranged in the second channel.

4. The method of claim 2, wherein the electrical signals are voltage pulses delivered into the medium, pulse amplitudes of which are acquired as the measurement values at the second microsystem component.

5. The method of claim 1, wherein the two microsystem components are displaced with respect to one another along at least two mutually orthogonal spatial axes, a first spatial axis extending approximately parallel to longitudinal axes of the two holes into a plane spanned by said two mutually orthogonal spatial axes.

6. The method of claim 5, wherein a rough relative position is determined along the first spatial axis by displacing the two microsystem components along the first spatial axis into different relative positions while maintaining a fixed relative position along the second spatial axis and taking a measurement value for each relative position.

7. The method of claim 6, wherein the fixed relative position along the second spatial axis is selected as a function of dimensions of the microsystem components in a direction of the second spatial axis, between the two microsystem components in the direction of the second spatial axis.

8. The method of claim 5, wherein a rough relative position is determined along a second spatial axis by displacing the two microsystem components along the second spatial axis into different relative positions while maintaining a fixed relative position along the first spatial axis and taking a measurement value for each relative position.

9. The method of claim 8, wherein the fixed relative position along the first spatial axis is determined as a function of the rough relative position along the first spatial direction, between the two holes in a direction of the first spatial axis.

10. The method of claim 8, wherein a finely resolved relative position is determined along the first spatial axis by displacing the two microsystem components along the first spatial axis into different relative positions while maintaining a rough relative position along the second spatial axis and taking a measurement value for each relative position.

11. The method of claim 10, wherein a finely resolved relative position is determined along the second spatial axis by displacing the two microsystem components along the second spatial axis into different relative positions while maintaining a finely resolved relative position along the first spatial axis and taking a measurement value for each relative position.

12. The method of claim 11, wherein the two microsystem components are displaced relative to one another along a third spatial axis which extends orthogonally to the first and second spatial axes, a relative position being determined in the third spatial axis by displacing the two microsystem components along the third spatial axis into different relative positions while maintaining a fixed relative position along the first and second spatial axes and taking a measurement value for each relative position.

13. The method of claim 1, wherein the first microsystem component is configured for immobilizing a biological cell and the second microsystem component is configured for contacting a cell immobilized in this way.

14. The method of claim 1, wherein a third microsystem component having a third hole is provided, and a relative position between the second and third holes is determined.

15. The method of claim 14, wherein the third microsystem component is mechanically connected to the first microsystem component.

16. The method of claim 12, wherein a third microsystem component having a third hole is provided, the third microsystem component being mechanically connected to the first microsystem component, and wherein the method further comprises:
   determining a relative position between the second and third holes.

17. A method for the automated contacting of at least one microscopic test object between two holes, one hole on each of a first and a second microsystem, the method comprising:
   A) determining a relative position between the two holes, utilizing electrical resistance as a measurement parameter
   B) immobilizing a microscopic test object on a first of the holes,
   C) aligning the two holes along a first spatial axis with a start distance at least two times a maximum diameter of the microscopic test object to be contacted,
   D) measuring a resistance in front of a second of the holes with a sensor electrode,
   E) reducing distance between the two holes along the first spatial axis by an amount, and
   F) repeating steps D) and E) until a predetermined change in the measured resistance in front of the second hole is detected indicting that a microscopic test object has been contacted.

18. The method of claim 17, wherein prior to mutually aligning of the first and second holes along said first spatial axis with said start distance, the test object is checked for suitability for subsequent examinations.

19. The method of claim 17, wherein the resistance in front of the first hole is measured by means of a sensor electrode during the immobilization of the test object on the first hole.

20. A device for the automated contacting of at least one microscopic test object which is immobilized on a first hole and is then contacted through a second hole, comprising:
- at least one first microsystem component, on which the first hole is provided,
- at least one second microsystem component, on which the second hole is provided,
- a reaction vessel for holding a liquid medium, the two microsystem components being immersed in the medium at least in the region of the holes,
- a mechanism for displacing the two microsystem components relative to one another at least in two mutually orthogonal spatial directions,
- a control device for controlling the mechanism for displacing in an automated fashion,
- and means for delivering electrical signals by one of the two microsystem components;
- means for recording the electrical signals on the other of the two microsystem components, measurement values of which depend on relative position of the two microsystem components with respect to one another,
- the control device being adapted to ascertain, from the measurement values for different relative positions between the two microsystem components, a relative position in which the two microsystem components are positioned so that their respective holes are mutually aligned.

21. The device of claim 20, wherein said first microsystem component is provided with a first channel opening in said first hole and said second microsystem component is provided with a second channel opening in said second hole.

* * * * *